United States Patent
Petereit et al.

(10) Patent No.: US 6,576,255 B1
(45) Date of Patent: Jun. 10, 2003

(54) INJECTION MOLDING METHOD FOR (METH)ACRYLATE COPOLYMERS HAVING TERTIARY AMMONIUM GROUPS

(75) Inventors: Hans-Ulrich Petereit, Darmstadt (DE); Thomas Beckert, Darmstadt (DE); Manfred Assmus, Bickenbach (DE); Werner Hoess, Heusenstamm (DE); Wolfgang Fuchs, Alsbach (DE); Hartmut Schikowsky, Darmstadt (DE)

(73) Assignee: Roehm GmbH & Co. KG, Darmstadt (DE)

( * ) Notice: Subject to any disclaimer, the term of this patent is extended or adjusted under 35 U.S.C. 154(b) by 1 day.

(21) Appl. No.: 09/889,565

(22) PCT Filed: Nov. 29, 2000

(86) PCT No.: PCT/EP00/11922
§ 371 (c)(1),
(2), (4) Date: Jul. 30, 2001

(87) PCT Pub. No.: WO01/39751
PCT Pub. Date: Jun. 7, 2001

(30) Foreign Application Priority Data

Dec. 2, 1999 (DE) .......................................... 199 58 007

(51) Int. Cl.⁷ ............................. A61K 9/48; A61K 9/58; B01J 13/02
(52) U.S. Cl. ........................ 424/451; 424/453; 424/452; 424/462; 264/4.1; 264/4.33
(58) Field of Search ................................. 424/400, 451, 424/452, 453, 462, 464, 465; 264/4.1, 4.33

(56) References Cited

U.S. PATENT DOCUMENTS

| | | | |
|---|---|---|---|
| 4,705,695 A | * | 11/1987 | Lehmann et al. ............... 427/3 |
| 5,548,033 A | * | 8/1996 | Vetter et al. ................. 525/378 |
| 5,705,189 A | * | 1/1998 | Lehmann et al. ............ 424/451 |
| 5,837,780 A | | 11/1998 | Albrecht et al. |
| 6,040,387 A | * | 3/2000 | Albrecht et al. ......... 525/330.5 |
| 6,287,470 B1 | | 9/2001 | Vetter et al. |

FOREIGN PATENT DOCUMENTS

| | | |
|---|---|---|
| EP | 0 704 207 | 4/1996 |
| EP | 0 727 205 | 8/1996 |
| GB | 1 298 084 | 11/1972 |
| GB | 1 355 324 | 6/1974 |

* cited by examiner

Primary Examiner—Thurman K. Page
Assistant Examiner—S. Tran
(74) Attorney, Agent, or Firm—Oblon, Spivak, McClelland, Maier & Neustadt, P.C.

(57) ABSTRACT

The invention relates to a process for making molded articles by means of injection molding with the process steps of a) melting of a (meth)acrylate copolymer, which is composed of 30 to 80 wt % of radical-polymerized C1 to C4 alkyl esters of acrylic or methacrylic acid and 70 to 20 wt % of (meth)acrylate monomers with a tertiary ammonium group in the alkyl residue, wherein the (meth)acrylate copolymer is present in a mixture with 1 to 70 wt % of a plasticizer and a desiccant in the ratio of 1:1 to 1:20 and also with 0.05 to 5 wt % of a release agent, and further standard additives or adjuvants and if necessary even a pharmaceutical active principle can also be present in the mixture, and before the mixture is melted it has a content of more than 0.5 wt % of low-boiling constituents with a vapor pressure of at least 1.9 bar at 120° C., b) degassing of the mixture in the thermoplastic condition at temperatures of at least 120° C., whereby the content of low-boiling constituents with a vapor pressure of at least 1.9 bar at 120° C. is lowered to at most 0.5 wt % and c) injection of the melted and degassed mixture into the mold cavity of an injection-molding die, wherein the mold cavity has a temperature which lies at least 10° C. below the glass transition temperature of the (meth)acrylate copolymer, cooling of the melt mixture and removal of the obtained molded article from the mold.

18 Claims, No Drawings

INJECTION MOLDING METHOD FOR (METH)ACRYLATE COPOLYMERS HAVING TERTIARY AMMONIUM GROUPS

This application is a 371 of PCT/EP00/11922 filed Nov. 29, 2000.

The invention relates to a process for manufacturing molded articles by means of injection molding, to the molded articles themselves and to their use for pharmaceutical purposes.

Prior Art

U.S. Pat. No. 4,705,695 describes a process for coating pharmaceutical formulations with an aqueous coating agent containing a water-soluble (meth)acrylate copolymer with tertiary amino groups as well as a water-insoluble, neutral polymer as binder. Solubility of the (meth)acrylate copolymer, which for example comprises equal proportions of methyl methacrylate and dimethylaminoethyl methacrylate, is achieved by stirring it in the form of powder with particle sizes smaller than 0.25 mm in water while simultaneously adding an acid. An insoluble copolymer, such as one of methyl methacrylate and ethyl acrylate (70:30) is used as binder. Preparation of the coating solution is relatively complex. Because of the acid content the coating has an unpleasant taste. Corresponding films dissolve both in synthetic gastric fluid and water in less than two minutes.

European Patent 0704207 A2 describes thermoplastic plastics for pharmaceutical coatings that are soluble in gastric fluid. They are copolymers of 16 to 40 wt % of acrylic or methacrylic acid, 30 to 80 wt % of methyl acrylate and 0 to 40 wt % of other alkyl esters of acrylic acid and/or methacrylic acid.

In the example, corresponding copolymers are melted at 160° C. and mixed after addition of 6 wt % of glycerol monostearate. The mixture is crushed and ground to a powder. The powder is filled into the tab of an injection-molding die and injected at 170° C. under a pressure of 150 bar through a 0.5 mm wide aperture into the mold cavity. After cooling there are obtained bubble-free, slightly opaque, thin-walled pharmaceutical capsules. Special measures for removal of low-boiling constituents immediately before processing by injection molding are not disclosed.

Object and Achievement

The object was considered to be to provide a process with which the known (meth)acrylate copolymers containing monomers with tertiary ammonium groups can be processed in the injection-molding process. In this way molded articles are supposed to be obtained that have properties of solubility in gastric fluid and that meet stringent mechanical requirements, and so can be used, for example, as capsules (locking capsules) which function as receptacles for pharmaceutical active principles.

A process for making molded articles by means of injection molding with the process steps of a) melting of a (meth)acrylate copolymer, which is composed of 30 to 80 wt % of radical-polymerized C1 to C4 alkyl esters of acrylic or methacrylic acid and 70 to 20 wt % of (meth)acrylate monomers with a tertiary ammonium group in the alkyl residue,
  wherein the (meth)acrylate copolymer is present in a mixture with 1 to 70 wt % of a plasticizer and a desiccant in the ratio of 1:1 to 1:20,
  wherein the plasticizer is present in a content of at least 1 wt %, and a release agent is present in a content of 0.05 to 5 wt % and further standard additives or adjuvants and if necessary a pharmaceutical active principle can also be present in the mixture, and before the mixture is melted it has a content of more than 0.5 wt % of low-boiling constituents with a vapor pressure of at least 1.9 bar at 120° C.

b) degassing of the mixture in the thermoplastic condition at temperatures of at least 120° C., whereby the content of low-boiling constituents with a vapor pressure of at least 1.9 bar at 120° C. is lowered to at most 0.5 wt % c) injection of the melted and degassed mixture into the mold cavity of an injection-molding die, wherein the mold cavity has a temperature which lies at least 10° C. below the glass transition temperature of the (meth)acrylate copolymer, cooling of the melt mixture and removal of the obtained molded article from the mold.

By means of the inventive process it is possible to obtain novel injection-molded articles that meet the requirements of high mechanical strength and high thermal stability.

Operation of the Invention

The inventive process for manufacture of molded articles by means of injection molding is divided into process steps a), b) and c).

Process Step a)

Melting of a (meth)acrylate copolymer, which is composed of 30 to 80 wt % of radical-polymerized C1 to C4 alkyl esters of acrylic or methacrylic acid and 70 to 20 wt % of (meth)acrylate monomers with a tertiary ammonium group in the alkyl residue, wherein the (meth)acrylate copolymer is present in a mixture with 1 to 70 wt % of a plasticizer and a desiccant in the ratio of 1:1 to 1:20, preferably 1:1 to 1:10, particularly preferably 1:1 to 1:4, wherein the plasticizer content is present in a content of at least 1 wt %, a release agent is present in a content of 0.05 to 5 wt %, preferably 0.1 to 3 wt % and further standard additives or adjuvants and if necessary a pharmaceutical active principle can also be present in the mixture, and before the mixture is melted it has a content of more than 0.5 wt % of low-boiling constituents with a vapor pressure of at least 1.9 bar at 120° C.

Melting of the copolymer, which has the form of granules or powder, takes place preferably in an extruder at a temperature of 80 to 250° C.

The (Meth)Acrylate Copolymer

The (meth)acrylate copolymer is composed of 30 to 80 wt % of radical-polymerized C1 to C4 alkyl esters of acrylic or methacrylic acid and 70 to 20 wt % of (meth)acrylate monomers with a tertiary ammonium group in the alkyl residue.

Suitable monomers with functional tertiary ammonium groups are listed in U.S. Pat. No. 4,705,695 column 3, line 64 to column 4, line 13. In particular, there can be cited dimethylaminoethyl acrylate, 2-dimethylaminopropyl acrylate, dimethylaminopropyl methacrylate, dimethylaminobenzyl acrylate, dimethylaminobenzyl methacrylate, (3-dimethylamino-2,2-dimethyl)propyl acrylate, dimethylamino-2,2-dimethyl)propyl methacrylate, (3-diethylamino-2,2-dimethyl)propyl acrylate and diethylamino-2,2-dimethyl)propyl methacrylate. Dimethylaminoethyl methacrylate is particularly preferred.

The content of monomers with tertiary ammonium groups in the copolymer can be advantageously between 20 and 70 wt %, preferably between 40 and 60 wt %. The proportions of the C1 to C4 alkyl esters of acrylic or methacrylic acid is 70 to 30 wt %. Examples are methyl methacrylate, ethyl methacrylate, butyl methacrylate, methyl acrylate, ethyl acrylate and butyl acrylate.

A suitable (meth)acrylate copolymer with tertiary amino groups can be formed, for example, from 20 to 30 wt % of methyl methacrylate, 20 to 30 wt % of butyl methacrylate and 60 to 40 wt % of dimethylaminoethyl methacrylate.

A specifically suitable commercial (meth)acrylate copolymer with tertiary amino groups is formed, for example, from 25 wt % of methyl methacrylate, 25 wt % of butyl methacrylate and 50 wt % of dimethylaminoethyl methacrylate (EUDRAGIT® E100).

The copolymers are obtained in ways known in themselves by radical bulk, solution, bead or emulsion polymerization. Before processing, their particle sizes must be reduced to the inventive range by suitable grinding, drying or spraying processes. This can be achieved by simple crushing of extruded and cooled strand for granules or by hot face cutting.

The use of powders can be advantageous in particular for mixing with other powders or liquids. Suitable apparatus for preparing powders are familiar to those skilled in the art. Examples are air-jet mills, rod mills and fan-type mills. If necessary, appropriate sieving steps can be included. A suitable mill for industrial-scale large quantities is, for example, a counter-jet mill (Multi No. 4200), which is operated with about 6 bar gauge pressure.

The average particle size of the powder form can be determined as follows:

By air-jet sieving for simple separation of the ground product into a few fractions. This method is somewhat less precise in this measurement range than are the alternatives. At least 70%, preferably 90% of the particles relative to the weight (weight distribution) must fall within the size range of 1 to 40 $\mu$m, preferably between 5 and 35, especially between 10 and 20 $\mu$m.

A highly suitable measurement method is laser diffraction for determination of the particle-size distribution. Commercial instruments permit measurement in air (S3.01 particle sizer of the Malvern Co.) or preferably in liquids (Galai CIS 1 of the LOT Co.). The prerequisite for measurement in liquid media is that the polymer does not dissolve therein or that the particles do not change in some other way during the measurement. A suitable medium is, for example, an aqueous Polysorbate 80 solution that has been highly diluted (to about 0.02%).

Mixtures

The (meth)acrylate copolymer is present in a mixture with 1 to 70 wt % of a plasticizer and a desiccant in the ratio of 1:1 to 1:20, preferably 1:1 to 1:10, particularly preferably 1:1 to 1:4. If necessary, the mixture can also contain further pharmaceutically common standard adjuvants, for example in a proportion of 0.001 wt % to 30 wt % relative to the (meth)acrylate copolymer.

To control the rate of release of active principle, it can be advantageous in the individual case to mix in further polymers. The proportion of further polymers in the mixture, however, does not exceed 20 wt %, preferably at most 10 wt %, especially 0 to 5 wt % relative to the (meth)acrylate copolymer.

Examples of such further polymers are: polyvinylpyrrolidone, polyvinyl alcohols, anionic (meth) acrylate copolymers of methyl methacrylate and/or ethyl acrylate and methacrylic acid (EUDRAGIT® L 100, EUDRAGIT® S 100, EUDRAGIT® L 100-55). Anionic (meth)acrylate copolymers of methyl methacrylate, methyl acrylate and methacrylic acid, carboxymethylcellulose salts, hydroxypropylcellulose (HPMC), neutral (meth)acrylate copolymers of methyl methacrylate and ethyl acrylate (dry substance of EUDRAGIT® NE 30 D), copolymers of methyl methacrylate and butyl methacrylate (PLASTOID® B) or (meth)acrylate copolymers with quaternary ammonium groups (EUDRAGIT® RL and EUDRAGIT® RS).

Furthermore, one or more pharmaceutical active principles that do not decompose at processing temperature can be present.

The pharmaceuticals used within the meaning of the invention are intended for administration on or in the human or animal body in order 1. to cure, alleviate, prevent or detect diseases, injuries, body damage or pathological conditions,
2. to allow the nature, condition or functions of the body or mental conditions to be discerned,
3. to replace active principles or body fluids generated by the human or animal body,
4. to combat, eliminate or render harmless pathogens, parasites or substances foreign to the body or
5. to influence the nature, condition or functions of the body or mental conditions.

Common pharmaceuticals can be found in reference works such as the Red List or the Merck Index.

According to the invention there can be used all active principles that satisfy the desired therapeutic effect within the meaning of the definition given hereinabove and that have adequate thermal stability as well as the ability to penetrate through the skin.

Without claiming completeness, important examples (groups and individual substances) are the following:

analgesics, antiallergics, antiarrhythmics antibiotics, chemotherapeutics, antidiabetics, antidotes, antiepileptics, antihypertensives, antihypotensives, anticoagulants, antimycotics, antiphlogistics, beta receptor blockers, calcium antagonists and ACE inhibitors, broncholytics/antiasthmatics, cholinergics, corticosteroids (internal), dermatics, diuretics, enzyme inhibitors, enzyme preparations and transport proteins, expectorants, geriatrics, gout remedies, flu medicines, hormones and their inhibitors, hypnotics/sedatives, cardiacs, lipid-lowering drugs, parathyroid hormones/calcium metabolism regulators, psychopharmaceuticals, sex hormones and their inhibitors, spasmolytics, sympatholytics, sympathomimetics, vitamins, wound medications, cytostatics.

Examples of active principles that are suitable for filling into the molded articles (capsules) or even for incorporation into the molded articles are: ranitidine, simvastatin, enalapril, fluoxetine, amlodipine, amoxicillin, sertaline, nifidipine, ciprofloxacin, acyclovir, lovastatin, epoetin, paroxetine, captopril, nabumetone, granisetron, cimetidine, ticarcillin, triamterene, hydrochlorothiazide, verapamil, paracetamol, morphine derivatives, topotecan or the pharmaceutically used salts.

Plasticizers: Substances suitable as plasticizers usually have a molecular weight of between 100 and 20,000 and contain one or more hydrophilic groups in the molecule, such as hydroxyl, ester or amino groups. Suitable groups are citrates, phthalates, sebacates, castor oil. Examples of suitable plasticizers are citric acid alkyl esters, glycerol esters, phthalic acid alkyl esters, sebacic acid alkyl esters, sucrose esters, sorbitan esters, dibutyl sebacate and polyethylene glycols 4000 to 20,000. Preferred plasticizers are tributyl citrate, triethyl citrate, acetyltriethyl citrate, dibutyl sebacate and diethyl sebacate. The proportions used range between 1 and 35, preferably between 2 and 10 wt % relative to the (meth)acrylate copolymer.

Desiccants (antiblocking agents): Desiccants have the following properties: they have large specific surfaces, are chemically inert, and are readily free-flowing and finely divided. By virtue of these properties they can be advantageously dispersed homogeneously in melts to lower the tackiness of polymers containing strongly polar comonomers as functional groups.

Examples of desiccants are:
aluminum oxide, magnesium oxide, kaolin, talc, silica gel (Aerosils), barium sulfate, carbon black and cellulose.
Release Agents (mold-release agents)

Mold-release agents must be added in a proportion of 0.05 wt % to 5, preferably 0.1 to 3 wt % relative to the copolymer.

In contrast to desiccants, mold-release agents have the property of reducing the adhesive force between the molded articles and the die surface in which the molded article is being made. Thereby it is possible to make molded articles which are not broken and are geometrically not deformed. Mold-release agents are mostly partly compatible or incompatible with the polymers in which they are particularly effective. By virtue of the partial compatibility or incompatibility, migration into the interface of the transition zone between die wall and molded article takes place during injection of the melt into the mold cavity.

To ensure that mold-release agents can migrate particularly advantageously, the melting point of the mold release agent must be 20° C. to 100° C. below the processing temperature of the polymer.

Examples of release agents (mold-release agents) are:
esters of fatty acids or fatty acid amides, aliphatic, long-chain carboxylic acids, fatty alcohols as well as their esters, montan or paraffin waxes and metal soaps. Worth special mention are glycerol monostearate, stearyl alcohol, glycerol behenic acid esters, cetyl alcohol, palmitic acid, carnauba wax, beeswax, etc.

Further pharmaceutically common adjuvants: Examples are stabilizers, coloring agents, antioxidants, cross-linking agents, pigments, brighteners, etc. They are used in particular as processing auxiliaries and are intended to ensure a reliable and reproducible manufacturing process as well as good long-term stability. Further pharmaceutically common adjuvants can be present in proportions of 0.001 wt % to 30 wt %, preferably 0.1 to 10 wt % relative to the copolymer.

Low-boiling Constituents

In its commercial form, the (meth)acrylate copolymer known in itself practically always has a content of more than 0.5 wt % of low-boiling constituents with a vapor pressure of at least 1.9 bar at 120° C. The usual contents of these constituents range from 0.7 to 2.0 wt %. The low-boiling constituents comprise mainly water, which is absorbed from atmospheric moisture.

Process Step b)

Degassing of the mixture at temperatures of at least 120° C., preferably at least 150° C. and at most 250° C., whereby the content of low-boiling constituents with a vapor pressure of at least 1.9 bar at 120° C. is lowered to at most 0.5 wt %, preferably at most 0.2 wt %, particularly preferably at most 0.1 wt %. Thereby it is possible to ensure that undesired sudden outgassing, which would lead to bubble formation or to foaming inside the molded article being formed, which would then become unusable, cannot occur during the injection-molding process in process step c).

Since the (meth)acrylate copolymer has a glass transition temperature in the range of 50° C., low-boiling constituents cannot be removed by simple drying at high temperature, since the copolymer would then undergo undesirable sintering or film formation.

Degassing step b) is therefore carried out preferably by extrusion drying by means of an extruder with degassing zone or by means of an injection-molding system with an injection-molding die with upstream degassing aperture.

The degassed extruded product obtained by extrusion drying in an extruder with degassing zone can be fed directly to the injection-molding machine, without further process steps for removal of low-boiling constituents, and processed directly to molded articles.

In the case of degassing on an injection-molding system with degassing opening present in the injection-molding cylinder, degassing by means of the said degassing aperture in the injection-molding cylinder takes place before the plastic melt is injected into the injection-molding mold.

Process Step c)

Injection of the melted and degassed mixture into the mold cavity of an injection-molding die, wherein the mold cavity has a temperature which lies at least 10° C., preferably at least 12° C., particularly preferably at least 15° C., especially at least 25° C. or even at least 35° C. below the glass transition temperature of the (meth)acrylate copolymer, cooling of the melt mixture and removal of the obtained molded article from the mold.

Thermoplastic processing takes place in a manner known in itself by means of an injection-molding machine at temperatures in the range of 80 to 20° C., especially between 120° C. and 160° C., and at pressures of 60 to 400 bar, preferably 80 bar to 120 bar.

Since the glass transition temperatures of the (meth) acrylate copolymers being used range, for example, from 40° C. to 80° C., the mold temperature is correspondingly lower. For example, it is at most 30 or at most 20° C., and so the copolymer already solidifies in the mold a short time after the injection process and the finished molded article can be removed or released from the mold.

The molded articles can be removed from the mold cavity of the injection-molding die without breakage, and they have a uniform, compact, flawless surface. The molded article is characterized by mechanical loadability or elasticity and ultimate tensile strength.

In particular, it has an impact strength of at least 1.0 kJ/m$^2$, preferably at least 1.5 kJ/m$^2$, particularly preferably of at least 2.0 kJ/m$^2$ according to ISO 179, as measured on test specimens.

The Vicat softening temperature VST (A10), measured on test specimens according to ISO 306, ranges between approximately 30° C. and 60° C.

The molded articles obtained according to the invention can have the form, for example, of a capsule, part of a capsule, such as a capsule half, or a locking capsule, which is used as a receptacle for a pharmaceutical active principle. Active principles contained in binders, for example, can be filled thereinto in the form of pellets, after which the two capsule parts are joined together by bonding with adhesive, by heat-sealing by laser, ultrasonic or microwave radiation, or by means of snap connection.

By means of this process, capsules of different material (such as gelatins, hydrolyzed starches, HPMC or other methacrylates) can be combined with one another according to the invention. Thus the molded article can also be part of a dosage unit.

Other forms such as tablet or lenticular geometries are also possible. In this connection the compound used for injection molding already contains the pharmaceutical active principle. In the final form the active principle is present in the most uniform possible distribution in crystalline form (solid dispersion) or dissolved form (solid solution).

EXAMPLES

Example 1

Molded Articles that are Soluble in Gastric Fluid/ Degassing in the Extruder

An inventive mixture (compound) was prepared in a twin-screw extruder (Leistritz LMS 30.34).

By means of a gravimetric proportioning device, granules of a methacrylate copolymer of 25 wt % of methyl methacrylate, 25 wt % of butyl methacrylate and 50 wt % of dimethylaminoethyl methacrylate (EUDRAGIT® E 100) were proportioned into the feed zone of the twin-screw extruder at a rate of 10 kg per hour. In addition, 20 wt % of talc (desiccant) as well as 0.25 wt % of stearyl alcohol (mold-release agent) was proportioned continuously into the feed zone of the twin-screw extruder through a further gravimetric proportioning device.

At a screw speed of 120 rpm, the components were fed into the extruder, the polymer was plasticized and the talc was mixed homogeneously into the melt. The adjusted melt temperature was 160° C. At a distance of 50% along the total length of the twin-screw extruder there is disposed in the cylinder wall an aperture through which triethyl citrate is pumped in by means of a diaphragm pump in a proportion of 5 wt % relative to the polymer quantity. Downstream from a mixing zone for homogenization of the mixture, there is disposed in the screw cylinder a degassing aperture, which is provided with an opening to the environment. It can be seen that steam emerges from the degassing zone.

By means of a nozzle, four strands were extruded from the extruder, drawn over a cooled metal sheet and chopped into granules. The moisture content of the obtained granules (determined by the K. Fischer method) was found to be 0.05%. A check of the non-extruded starting granules yielded 0.94% water.

To improve the free-flowing ability and to reduce the tackiness, the granules were intensively mixed in a mixing drum after addition of 0.05% of talc, and so the individual granules had a powdered surface.

Processing of the Obtained Granules by Injection Molding:

The obtained mixture (compound) was fed into the hopper of an injection-molding machine (Arburg Allrounder 221-55-250) and molded articles were obtained by injection molding.

The following temperatures were adjusted on the injection-molding machine: zone 1 (feed zone): 70° C., zone 2: 120° C., zone 3: 160° C, zone 4: 160° C., zone 5 (nozzle): 130° C. Injection pressure 60 bar, holding pressure 50 bar, dynamic pressure 5 bar, die temperature 17° C.

A plate measuring 60×45×1 mm was injection-molded as the molded article. Plates free of streaks, with flawless smooth surface were obtained. The plates were removed from the mold without problem and are dimensionally stable.

Example 2

(Comparison Example)

A compound was prepared as described in Example 1, except that the degassing aperture at the end of the extruder was closed. A moisture content of 0.63% was determined on the granules obtained from the extruder.

The granules were fed to the injection-molding machine as in Example 1, and processed with the same parameter settings.

The obtained molded articles exhibited streaks and surface flaws, and were not in conformity with the requirements.

After 7 molded articles had been made, problems developed with the granulate feed unit on the injection-molding machine. It was observed that condensed moisture had collected in the feed zone of the screw, leading to interruption of the delivery of solids.

Example 3

(Comparison Example/Without Desiccant)

A mixture was prepared as described in Example 1, except that 0.25 wt % of stearyl alcohol was added alone, without desiccant. The obtained granules were fed to the injection-molding machine and processed as described in Example 1. It was not possible to make a molded article. The plate sticks in the injection-molding die and cannot be removed from the mold.

Example 4

Degassing on an Injection-molding Machine

A mixture (compound) was prepared as described in Example 1, except that the degassing aperture was closed. A moisture content of 0.57% was determined on the obtained granules by the K. Fischer method. On the injection-molding machine, the injection-molding unit was replaced by a unit with a degassing aperture in the screw cylinder.

The granules were processed to molded articles without problems.

Example 5

A mixture was prepared as specified in Example 1. On an injection-molding machine (model: Boy micro 22), injection molding was performed with an injection-molding die for capsules with a length of 16 mm, an average outside diameter of 6.8 mm, tapering to 4 mm at the closed end, and a wall thickness of 0.6 mm.

After injection of the melt, a holding time of 6 seconds and then a cooling time of 18 seconds, the die was opened and the capsules removed from the mold. The capsules were removed from the mold of the die without breakage. Mechanically stable capsules with an opaque to whitish color were obtained.

Test of the Solubility of the Produced Capsules in Gastric Fluid

The dissolution behavior of the produced capsules was tested according to the European Pharmacopoeia in a paddle-type apparatus with a speed of 100 rpm. The capsule dissolved in synthetic gastric fluid (0.1 N hydrochloric acid, pH 1.2) after 2 hours. In demineralized water, only slight swelling associated with whitish cloudiness was observed, while no change was observed after 2 hours in phosphate buffer with pH 7.5.

What is claimed is:

1. A process for making a molded article, comprising:
   a) melting a mixture comprising
      A1) a (meth)acrylate copolymer, which comprises 1) 30 to 80 wt % of a radical-polymerized C1 to C4 alkyl ester of acrylic or methacrylic acid and 2) 70 to 20 wt % of a (meth)acrylate monomer having a tertiary ammonium group in an alkyl residue;
      A2) 1 to 70 wt % of a plasticizer and a desiccant in a ratio of 1:1 to 1:20; wherein said plasticizer is present in an amount of at least 1 wt %;
      A3) 0.05 to 5 wt % of a release agent;
      A4) an additive or adjuvant; and
      A5) optionally a pharmaceutical active principle, to obtain a melted mixture;
         wherein, before said melting, said mixture has a content of more than 0.5 wt % of low-boiling constituents with a vapor pressure of at least 1.9 bar at 120° C.;
   b) degassing said melted mixture in a thermoplastic condition at a temperature temperatures of at least 120° C., whereby said content of low-boiling constituents with a vapor pressure of at least 1.9 bar at 120° C. is lowered to not more than 0.5 wt %, to obtain a degassed mixture;
   c) injecting said degassed mixture into a mold cavity of an injection-molding die, to obtain a molded mixture;
      wherein said mold cavity has a temperature which is at least 10° C. below a glass transition temperature of said (meth)acrylate copolymer;
   d) cooling of said molded mixture, to obtain a molded article; and
   e) removal of said molded article from said injection-molding die.

2. The process according to claim 1, wherein said degassing is carried out by extrusion drying using an extruder with a degassing zone or using an injection-molding system with a degassing aperture in an injection-molding cylinder, upstream from said injection-molding die.

3. An injection-molded article obtained by a process according to claim 1.

4. The molded article according to claim 3, which has an impact strength of at least 1.5 kJ/m$^2$.

5. The molded article according to claim 3, which is a capsule, a part of a capsule or a part of a dosage unit.

6. The molded article according to claim 3, wherein the article contains a pharmaceutical active principle.

7. A receptacle or a vehicle for a pharmaceutical active principle, comprising the molded article according to claim 3.

8. The process according to claim 1, wherein said ratio of said plasticizer to said desiccant is 1:1 to 1:10.

9. The process according to claim 1, wherein said ratio of said plasticizer to said desiccant is 1:1 to 1:4.

10. The process according to claim 1, wherein said mixture comprises 0.1 to 3 wt % of said release agent.

11. The process according to claim 1, wherein said melting is at a temperature of from 80 to 250° C.

12. The process according to claim 1, wherein said (meth)acrylate monomer having the tertiary ammonium group is selected from the group consisting of dimethylaminoethyl acrylate, 2-dimethylaminopropyl acrylate, dimethylaminopropyl methacrylate, dimethylaminobenzyl acrylate, dimethylaminobenzyl methacrylate, (3-dimethylamino-2,2-dimethyl)propyl acrylate, dimethylamino-2,2-dimethyl)propyl methacrylate, (3-diethylamino-2,2-dimethyl)propyl acrylate and diethylamino-2,2-dimethyl)propyl methacrylate.

13. The process according to claim 1, wherein said (meth)acrylate copolymer comprises 40 to 60 wt % of said (meth)acrylate monomer having the tertiary ammonium group.

14. The process according to claim 1, wherein said (meth)acrylate copolymer comprises 20 to 30 wt % of methyl methacrylate, 20 to 30 wt % of butyl methacrylate and 60 to 40 wt % of dimethylaminoethyl methacrylate.

15. The process according to claim 1, wherein said (meth)acrylate copolymer is in the form of a powder and at least 70% of the particles relative to the weight fall within the size range of 1 to 40 µm.

16. The process according to claim 1, wherein said desiccant is selected from the group consisting of aluminum oxide, magnesium oxide, kaolin, talc, silica gel, barium sulfate, carbon black and cellulose.

17. The process according to claim 1, wherein said low boiling constituent is water.

18. The process according to claim 1, wherein a glass transition temperature of said (meth)acrylate copolymer is from 40 to 80° C.

* * * * *